United States Patent
Clark et al.

(10) Patent No.: US 9,474,516 B2
(45) Date of Patent: Oct. 25, 2016

(54) HANDLE ASSEMBLY FOR A LEFT ATRIAL APPENDAGE OCCLUSION DEVICE

(71) Applicant: BOSTON SCIENTIFIC SCIMED, INC., Maple Grove, MN (US)

(72) Inventors: Christopher Clark, St. Michael, MN (US); Brian Tischler, New Brighton, MN (US); Mark McPhail, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 377 days.

(21) Appl. No.: 13/670,676

(22) Filed: Nov. 7, 2012

(65) Prior Publication Data

US 2013/0116724 A1    May 9, 2013

Related U.S. Application Data

(60) Provisional application No. 61/557,123, filed on Nov. 8, 2011.

(51) Int. Cl.
*A61F 11/00* (2006.01)
*A61B 17/00* (2006.01)
*A61B 17/12* (2006.01)

(52) U.S. Cl.
CPC .... *A61B 17/0057* (2013.01); *A61B 2017/0046* (2013.01); *A61B 2017/0053* (2013.01); *A61B 2017/00243* (2013.01); *A61B 2017/00575* (2013.01); *A61B 2017/00623* (2013.01); *A61B 2017/1205* (2013.01)

(58) Field of Classification Search
CPC ..... A61F 2/013; A61F 2/95; A61B 17/0057; A61B 2017/1205; A61B 2017/00243; A61B 2017/00575; A61B 2017/0053; A61B 2017/00623; A61B 2017/0046
USPC ................................. 606/108, 200; 623/1.11
See application file for complete search history.

(56) References Cited

U.S. PATENT DOCUMENTS

| | | |
|---|---|---|
| 178,283 A | 6/1876 | French |
| 1,967,318 A | 7/1934 | Monahan |
| 3,844,302 A | 10/1974 | Klein |
| 3,874,388 A | 4/1975 | King et al. |
| 4,007,743 A | 2/1977 | Blake |

(Continued)

FOREIGN PATENT DOCUMENTS

| WO | 9313712 A1 | 7/1993 |
|---|---|---|
| WO | 9721402 A1 | 6/1997 |

(Continued)

OTHER PUBLICATIONS

US 4,932,055, 06/1990, Palestrant (withdrawn)

(Continued)

*Primary Examiner* — Richard Louis
(74) *Attorney, Agent, or Firm* — Seager, Tufte & Wickhem LLP (57) ABSTRACT

The disclosure pertains to a handle assembly for a left atrial appendage occlusion device delivery system and methods of use therefor. The handle assembly includes a leadscrew mechanism for smooth, low backlash control of a delivery catheter for the left atrial appendage occlusion device and manipulation segments which allow one hand operation of the handle assembly.

13 Claims, 6 Drawing Sheets

(56) References Cited

U.S. PATENT DOCUMENTS

| | | |
|---|---|---|
| 4,341,218 A | 7/1982 | U |
| 4,585,000 A | 4/1986 | Hershenson |
| 4,603,693 A | 8/1986 | Conta et al. |
| 4,665,906 A | 5/1987 | Jervis |
| 4,710,192 A | 12/1987 | Liotta et al. |
| 4,873,978 A | 10/1989 | Ginsburg |
| 4,917,089 A | 4/1990 | Sideris |
| 4,921,484 A | 5/1990 | Hillstead |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,078,736 A | 1/1992 | Behl |
| 5,108,420 A | 4/1992 | Marks |
| 5,171,259 A | 12/1992 | Inoue |
| 5,171,383 A | 12/1992 | Sagae et al. |
| 5,176,692 A | 1/1993 | Wilk et al. |
| 5,192,301 A | 3/1993 | Kamiya et al. |
| 5,256,146 A | 10/1993 | Ensminger et al. |
| 5,258,042 A | 11/1993 | Mehta |
| 5,284,488 A | 2/1994 | Sideris |
| 5,306,234 A | 4/1994 | Johnson |
| 5,334,217 A | 8/1994 | Das |
| 5,350,399 A | 9/1994 | Erlebacher et al. |
| 5,353,784 A | 10/1994 | Nady-Mohamed |
| 5,370,657 A | 12/1994 | Irie |
| 5,375,612 A | 12/1994 | Cottenceau et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,292 A | 7/1997 | Hart |
| 5,649,953 A | 7/1997 | Lefebvre |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,702,421 A | 12/1997 | Schneidt |
| 5,709,224 A | 1/1998 | Behl et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,735,290 A | 4/1998 | Sterman et al. |
| 5,749,883 A | 5/1998 | Halpern |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,810,874 A | 9/1998 | Lefebvre |
| 5,823,198 A | 10/1998 | Jones et al. |
| 5,824,055 A * | 10/1998 | Spiridigliozzi et al. ...... 623/1.11 |
| 5,830,228 A | 11/1998 | Knapp et al. |
| 5,836,913 A | 11/1998 | Orth et al. |
| 5,836,968 A | 11/1998 | Simon et al. |
| 5,846,260 A | 12/1998 | Maahs |
| 5,846,261 A | 12/1998 | Kotula et al. |
| 5,849,005 A | 12/1998 | Garrison et al. |
| 5,851,232 A | 12/1998 | Lois |
| 5,855,597 A | 1/1999 | Jayaraman |
| 5,865,791 A | 2/1999 | Whayne et al. |
| 5,865,802 A | 2/1999 | Yoon et al. |
| 5,868,702 A | 2/1999 | Stevens et al. |
| 5,868,708 A | 2/1999 | Hart et al. |
| 5,876,367 A | 3/1999 | Kaganov et al. |
| 5,882,340 A | 3/1999 | Yoon |
| 5,885,258 A | 3/1999 | Sachdeva et al. |
| 5,895,399 A | 4/1999 | Barbut et al. |
| 5,902,289 A | 5/1999 | Swartz et al. |
| 5,904,703 A | 5/1999 | Gilson |
| 5,906,207 A | 5/1999 | Shen |
| 5,906,619 A * | 5/1999 | Olson et al. ............... 606/108 |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,928,192 A | 7/1999 | Maahs |
| 5,928,260 A | 7/1999 | Chin et al. |
| 5,931,818 A | 8/1999 | Werp et al. |
| 5,935,112 A * | 8/1999 | Stevens et al. ............... 604/256 |
| 5,935,147 A | 8/1999 | Kensey et al. |
| 5,935,148 A | 8/1999 | Villar et al. |
| 5,941,249 A | 8/1999 | Maynard |
| 5,944,738 A | 8/1999 | Amplatz et al. |
| 5,947,997 A | 9/1999 | Pavcnik et al. |
| 5,951,589 A | 9/1999 | Epstein et al. |
| 5,954,694 A | 9/1999 | Sunseri |
| 5,957,940 A | 9/1999 | Tanner et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,068,621 A | 5/2000 | Balceta et al. |
| 6,074,357 A | 6/2000 | Kaganov et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,132,438 A | 10/2000 | Fleischman et al. |
| 6,136,016 A | 10/2000 | Barbut et al. |
| 6,139,527 A | 10/2000 | Laufer et al. |
| 6,152,144 A | 11/2000 | Lesh et al. |
| 6,161,543 A | 12/2000 | Cox et al. |
| 6,193,739 B1 | 2/2001 | Chevillon et al. |
| 6,231,561 B1 * | 5/2001 | Frazier et al. ............... 604/500 |
| 6,231,589 B1 | 5/2001 | Wessman et al. |
| 6,328,755 B1 | 12/2001 | Marshall |
| 6,533,782 B2 | 3/2003 | Howell et al. |
| 6,589,214 B2 | 7/2003 | McGuckin et al. |
| 6,650,923 B1 | 11/2003 | Lesh et al. |
| 6,755,812 B2 | 6/2004 | Peterson et al. |
| 7,044,134 B2 | 5/2006 | Khairkhahan et al. |
| 7,152,605 B2 | 12/2006 | Khairkhahan et al. |
| 7,192,439 B2 | 3/2007 | Khairkhahan et al. |
| 7,597,704 B2 | 10/2009 | Frazier et al. |
| 7,713,282 B2 | 5/2010 | Frazier et al. |
| 7,735,493 B2 | 6/2010 | van der Burg et al. |
| 7,972,359 B2 | 7/2011 | Kreidler |
| 8,043,329 B2 | 10/2011 | Khairkhahan et al. |
| 8,052,715 B2 | 11/2011 | Quinn et al. |

(56) References Cited

U.S. PATENT DOCUMENTS

| | | | |
|---|---|---|---|
| 8,287,563 | B2 | 10/2012 | Khairkhahan et al. |
| 8,323,309 | B2 | 12/2012 | Khairkhahan et al. |
| 2001/0027322 | A1* | 10/2001 | Bowman .................. 606/104 |
| 2002/0111647 | A1 | 8/2002 | Khairkhahan et al. |
| 2002/0111666 | A1* | 8/2002 | Hart et al. ................. 623/1.11 |
| 2003/0181942 | A1 | 9/2003 | Sutton et al. |
| 2003/0195555 | A1 | 10/2003 | Khairkhahan et al. |
| 2003/0199923 | A1 | 10/2003 | Khairkhahan et al. |
| 2003/0204203 | A1 | 10/2003 | Khairkhahan et al. |
| 2003/0212432 | A1 | 11/2003 | Khairkhahan et al. |
| 2003/0220667 | A1 | 11/2003 | van der Burg et al. |
| 2004/0044361 | A1 | 3/2004 | Frazier et al. |
| 2004/0127912 | A1* | 7/2004 | Rabkin et al. ............. 606/108 |
| 2004/0215230 | A1 | 10/2004 | Frazier et al. |
| 2005/0038470 | A1 | 2/2005 | van der Burg et al. |
| 2005/0154404 | A1* | 7/2005 | Liddicoat et al. .......... 606/139 |
| 2006/0020271 | A1 | 1/2006 | Stewart et al. |
| 2006/0206148 | A1 | 9/2006 | Khairkhahan et al. |
| 2007/0066993 | A1 | 3/2007 | Kreidler |
| 2007/0129753 | A1 | 6/2007 | Quinn et al. |
| 2007/0135826 | A1 | 6/2007 | Zaver et al. |
| 2008/0033457 | A1 | 2/2008 | Francischelli et al. |
| 2009/0099647 | A1 | 4/2009 | Glimsdale et al. |
| 2009/0143791 | A1 | 6/2009 | Miller et al. |
| 2009/0157118 | A1 | 6/2009 | Miller et al. |
| 2010/0114017 | A1* | 5/2010 | Lenker et al. ............. 604/96.01 |
| 2010/0145361 | A1 | 6/2010 | Francischelli et al. |
| 2010/0191279 | A1* | 7/2010 | Kassab et al. ............. 606/213 |
| 2010/0204716 | A1 | 8/2010 | Stewart et al. |
| 2011/0257718 | A1 | 10/2011 | Argentine |
| 2012/0029553 | A1 | 2/2012 | Quinn et al. |
| 2012/0035643 | A1 | 2/2012 | Khairkhahan et al. |
| 2012/0143301 | A1 | 6/2012 | Maslanka et al. |
| 2012/0239077 | A1 | 9/2012 | Zaver et al. |
| 2012/0239083 | A1 | 9/2012 | Kreidler |
| 2012/0271337 | A1 | 10/2012 | Figulla et al. |
| 2012/0276075 | A1 | 11/2012 | Fung et al. |
| 2012/0323262 | A1 | 12/2012 | Ibrahim et al. |
| 2013/0006343 | A1* | 1/2013 | Kassab ...................... 623/1.11 |

FOREIGN PATENT DOCUMENTS

| | | |
|---|---|---|
| WO | 9726939 A1 | 7/1997 |
| WO | 9728749 A1 | 8/1997 |
| WO | 9802100 A1 | 1/1998 |
| WO | 9817187 A1 | 4/1998 |
| WO | 9823322 A1 | 6/1998 |
| WO | 9907289 A1 | 2/1999 |
| WO | 9908607 A1 | 2/1999 |
| WO | 9930640 A1 | 6/1999 |
| WO | 9959479 A1 | 11/1999 |
| WO | 0001308 A1 | 1/2000 |
| WO | 0027292 A1 | 5/2000 |
| WO | 0053120 A1 | 9/2000 |
| WO | 0121247 A1 | 3/2001 |
| WO | 0126726 A1 | 4/2001 |
| WO | 0130266 A1 | 5/2001 |
| WO | 2004021930 A1 | 3/2004 |
| WO | 2011049808 A1 | 4/2011 |

OTHER PUBLICATIONS

Cragg et al., "A New Percutaneous Vena Cava Filter", ALJ, 141: 601-604, Sep. 1983.

Cragg et al., "Nonsurgical Placement of Arterial Endoprosthesis: A New Technique Using Nitinol Wire," Radiology, vol. 147, No. 1, pp. 261-263, Apr. 1983.

Lock et al., "Transcatheter Closure of Atrial Septal Defects," Circulation, vol. 79, No. 5, 1091-1099, May 1989.

Lock et al., "Transcatheter Umbrella Closure of Congenital Heart Defects," Circulation, vol. 75, No. 3, 593-599, 1987.

Rashkind et al., "Nonsurgical Closure of patent ductus arteriosus: clinical application of the Rashkind PDA Occluder System," Circulation, vol. 75, No. 3, 583-592, 1987.

Ruttenberg, "Nonsurgical Therapy of Cardiac Disorders," Pediatric Consult, vol. 5, No. 2, pages not numbered, 1986.

Sugita et al., "Nonsurgical Implantation of a Vascular Ring Prosthesis Using Thermal Shape Memory Ti/Ni Alloy (Nitinol Wire)," Trans. Am. Soc. Artif. Intern. Organs, vol. XXXII, 30-34, 1986.

Wessel et al., "Outpatient Closure of the patent ductus arteriosus," Circulation, vol. 77, No. 5, 1068-1071, 1988.

* cited by examiner

HANDLE ASSEMBLY FOR A LEFT ATRIAL APPENDAGE OCCLUSION DEVICE

BACKGROUND

Embolic stroke is the nation's third leading killer for adults, and is a major cause of disability. There are over 700,000 strokes per year in the United States alone. Of these, roughly 100,000 are hemorragic, and 600,000 are ischemic (either due to vessel narrowing or to embolism). The most common cause of embolic stroke emanating from the heart is thrombus formation due to atrial fibrillation. Approximately 80,000 strokes per year are attributable to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in part, to the fear of a stroke, and the pharmaceutical regimen necessary to reduce that risk.

For patients who develop atrial thrombus from atrial fibrillation, the clot normally occurs in the left atrial appendage (LAA) of the heart. The LAA is a cavity which looks like a small finger or windsock and which is connected to the lateral wall of the left atrium between the mitral valve and the root of the left pulmonary vein. The LAA normally contracts with the rest of the left atrium during a normal heart cycle, thus keeping blood from becoming stagnant therein, but often fails to contract with any vigor in patients experiencing atrial fibrillation due to the discoordinate electrical signals associated with AF. As a result, thrombus formation is predisposed to form in the stagnant blood within the LAA.

Blackshear and Odell have reported that of the 1288 patients with non-rheumatic atrial fibrillation involved in their study, 221 (17%) had thrombus detected in the left atrium of the heart. Blackshear J L, Odell J A., Appendage Obliteration to Reduce Stroke in Cardiac Surgical Patients With Atrial Fibrillation. Ann Thorac. Surg., 1996.61(2)755-9. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke in those patients.

Pharmacological therapies for stroke prevention such as oral or systemic administration of warfarin or the like have been inadequate due to serious side effects of the medications and lack of patient compliance in taking the medication. Invasive surgical or thorascopic techniques have been used to obliterate the LAA, however, many patients are not suitable candidates for such surgical procedures due to a compromised condition or having previously undergone cardiac surgery. In addition, the perceived risks of even a thorascopic surgical procedure often outweigh the potential benefits. See Blackshear and Odell, above. See also Lindsay B D., Obliteration of the Left Atrial Appendage: A Concept Worth Testing, Ann Thorac. Surg., 1996.61(2):515.

Despite the various efforts in the prior art, there remains a need for a minimally invasive method and associated devices for reducing the risk of thrombus formation in the left atrial appendage.

SUMMARY

This disclosure pertains to a handle assembly for a left atrial appendage occlusion device delivery system comprising a first non-rotating catheter displacement component rotatably connected to a second rotatable catheter displacement component, said a first non-rotating catheter displacement component having a distal end adapted to operably connect to a delivery catheter for a left atrial appendage occlusion device, wherein the first non-rotating catheter displacement component and the second rotatable catheter displacement component further comprise a lumen therethrough, further wherein the second rotatable catheter displacement component portion of the lumen comprises an internally threaded segment; a first manipulation segment having a externally threaded tubular distal extension adapted to rotationally engage the internally threaded segment of the second rotatable catheter displacement component, said externally threaded tubular distal extension having a length; and a second manipulation segment reversibly coupled to the first manipulation segment, wherein the second manipulation segment has affixed thereto an elongate shaft adapted to slidably and rotatably pass through a lumen associated with the first manipulation segment, the lumen of the first non-rotating catheter displacement component and second rotatable catheter displacement component, and a connected delivery catheter for a left atrial appendage occlusion device, further wherein rotation of the second rotatable catheter displacement component relative to the first non-rotating catheter displacement component is adapted to displace the delivery catheter proximally relative to the elongate shaft by a distance at least equal to the length of the externally threaded tubular distal extension of the first manipulation segment.

This disclosure also pertains to a method of using a handle assembly for a left atrial appendage occlusion device delivery system comprising connecting a handle assembly for a left atrial appendage occlusion device delivery system comprising: a first non-rotating catheter displacement component having a distal end adapted to operably connect to a delivery catheter for a left atrial appendage occlusion device; a second rotatable catheter displacement component; a first manipulation segment having an externally threaded tubular distal extension; and a second manipulation segment having affixed thereto an elongate shaft adapted to slidably and rotatably pass through a lumen associated with the first manipulation segment, a lumen to the first non-rotating catheter displacement component and second rotatable catheter displacement component, and a connected delivery catheter for a left atrial appendage occlusion device, to a delivery catheter for a left atrial appendage occlusion device at the distal end of the first non-rotating catheter displacement component of the handle assembly; positioning the distal end of the externally threaded tubular distal extension of the first manipulation segment proximate the distal end of the first non-rotating catheter displacement component such that a distal end of the elongate shaft extends beyond a distal end of the delivery catheter for a left atrial appendage occlusion device; reversibly attaching a left atrial appendage occlusion device to the distal end of the elongate shaft; withdrawing the left atrial appendage occlusion device into a distal end region of the delivery catheter for a left atrial appendage occlusion device adapted to contain a left atrial appendage occlusion device by moving the externally threaded tubular distal extension of the first manipulation segment proximally relative to the first non-rotating catheter displacement component and rotating the second rotatable catheter displacement component relative to the first non-rotating catheter displacement component.

This disclosure further pertains to a second method of using a handle assembly for a left atrial appendage occlusion device delivery system comprising inserting a delivery catheter for a left atrial appendage occlusion device intravascularly into a patient, wherein the delivery catheter has operably attached to its proximal end a handle assembly for a left atrial appendage occlusion device delivery system comprising a first non-rotating catheter displacement component having a distal end adapted to operably connect to a delivery catheter for a left atrial appendage occlusion device; a second rotatable catheter displacement component; a first manipulation segment having an externally threaded tubular distal extension; and a second manipulation segment having affixed thereto an elongate shaft adapted to slidably and rotatably pass through a lumen associated with the first manipulation segment, a lumen to the first non-rotating catheter displacement component and second rotatable catheter displacement component, wherein the delivery catheter for a left atrial appendage occlusion device further includes a collapsed left atrial appendage occlusion device disposed within a distal end region thereof, further wherein the left atrial appendage occlusion device is releasably connected to the elongate shaft; advancing the delivery catheter for a left atrial appendage occlusion device intravascularly until the left atrial appendage occlusion device is positioned at least partially within a left atrial appendage; rotating the second rotatable catheter displacement component relative to the first non-rotating catheter displacement component to withdraw the distal end region of the delivery catheter for a left atrial appendage occlusion device from left atrial appendage occlusion device thereby deploying the left atrial appendage occlusion device within the left atrial appendage; uncoupling the second manipulation segment reversibly coupled to the first manipulation segment from the first manipulation segment; manipulating the second manipulation segment to detach the left atrial appendage occlusion device from the distal end of the elongate shaft; and removing the delivery catheter for a left atrial appendage occlusion device from the patient.

DETAILED DESCRIPTION

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described unless clearly stated to the contrary.

Figure 1:
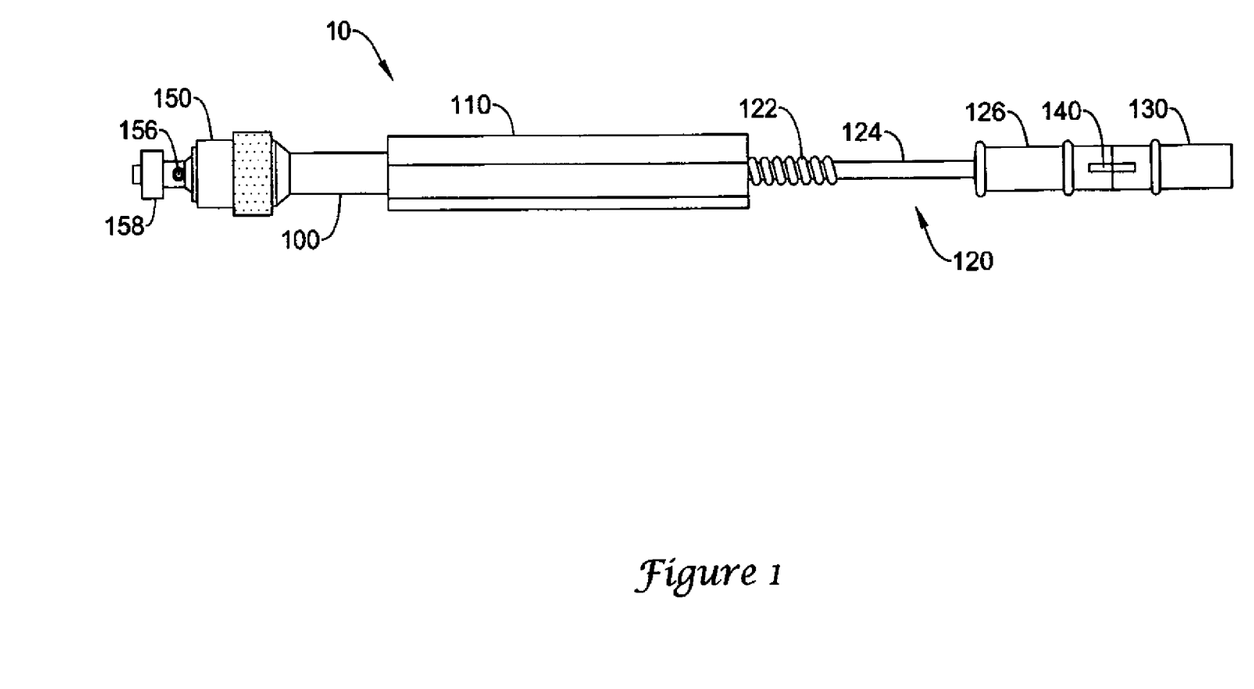
FIG. 1 illustrates a handle assembly for a left atrial appendage occlusion device delivery system in a first configuration.
Figure 2:
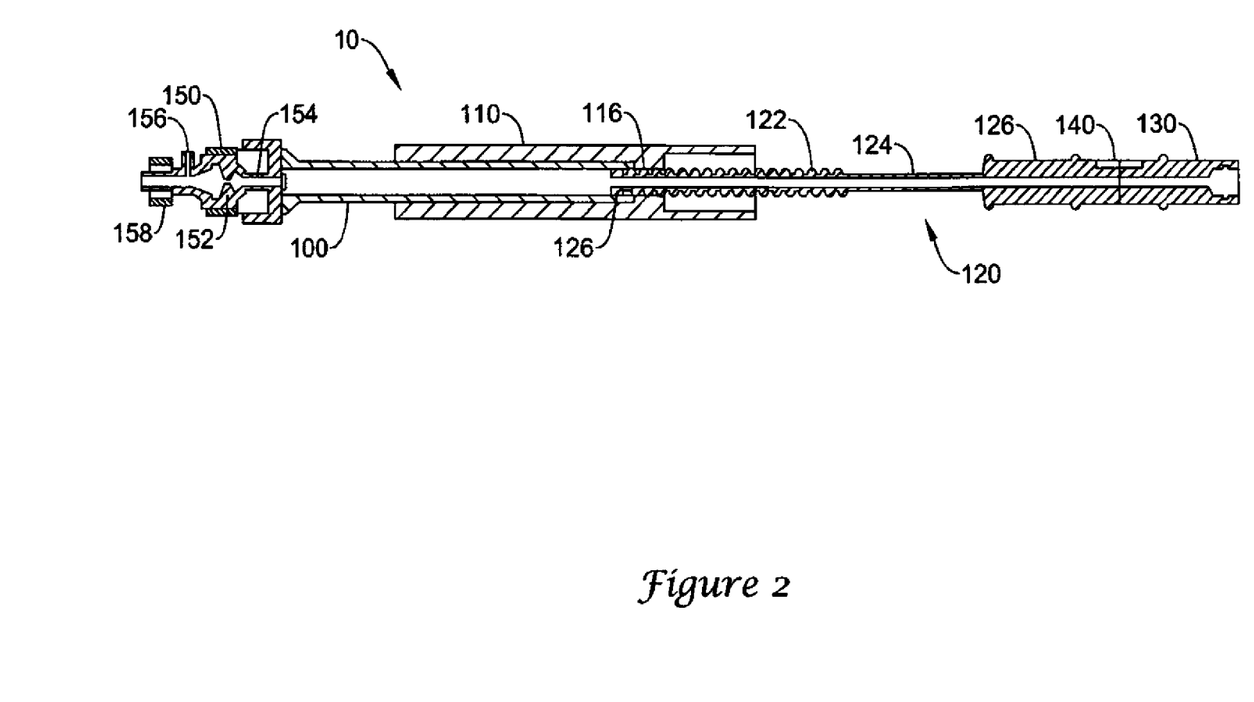
FIG. 2 illustrates the handle assembly of FIG. 1 in longitudinal cross-section.

FIGS. 1 and 2, shows a handle assembly 10 for a left atrial appendage occlusion device delivery system in a first configuration. The handle assembly comprises a first non-rotating catheter displacement component 100 rotatably connected to a second rotatable catheter displacement component 110, said a first non-rotating catheter displacement component 100 having a distal end adapted to operably connect to a delivery catheter (see element 160 of FIG. 5) for known left atrial appendage occlusion devices (not shown). The connection between the handle assembly and the delivery catheter for a left atrial appendage occlusion device may be made by any of the devices known in the art for that purpose, such as a Luer connector, and may be made with intervening elements if desired. The first non-rotating catheter displacement component 100 is joined to the second rotatable catheter displacement component 110 in a manner which allows relative rotation without significant longitudinal translation. A non-limiting example of such a join will be discussed with reference to FIG. 4C.

In some embodiments, the distal end of the first non-rotating catheter displacement component 100 may be connected to a hemostasis seal 150 to be discussed in greater detail. In such embodiments, the delivery catheter for a left atrial appendage occlusion device 100 may be connected to the distal end of the hemostasis seal 150 by any of the devices known in the art for that purpose, such as a Luer connector, and may be made with intervening elements if desired.

The first non-rotating catheter displacement component 100 may include a lumen, shared by proximal extension with the second rotatable catheter displacement component 110. The lumen is adapted to receive a distal portion of a first manipulation segment 120 which comprises a distal end 126, a externally threaded tubular distal extension 122, and a tubular segment 124 affixed to a proximal end of the externally threaded tubular distal extension 122. In some embodiments, the tubular segment 124 of first manipulation segment 120 includes an enlarged region 126 which facilitates manipulation of the handle during use. In other embodiments, the enlarged region 126 may be directly attached to the externally threaded tubular distal extension 122.

The externally threaded tubular distal extension 122 of first manipulation segment 120 is adapted to engage an internally threaded segment 116 of the second rotatable catheter displacement component 110 such that rotation of the second rotatable catheter displacement component 110 translates the first non-rotating catheter displacement component 100, and the second rotatable catheter displacement component 110 rotatably joined thereto, relative to the first manipulation segment 120. At least a portion of the lumen within the first non-rotating catheter displacement component 100 includes one or more keyways 102, best seen in FIGS. 4A-4D, which may engage one or more keys 128 associated with distal end 126 of first manipulation segment 120. The key(s) 128 and keyway(s) 102 cooperate to prevent rotation of the first non-rotating catheter displacement component 100 relative to first manipulation segment 120 as second rotatable catheter displacement component 110 is rotated relative to the first non-rotating catheter displacement component 100 and first manipulation segment 120. This allows an operator to grasp the first manipulation segment 120 with, for example the third and fourth fingers of one hand while rotating the second rotatable catheter displacement component 110 with the thumb and first finger of that hand for smooth retraction of the delivery catheter 160 (see FIG. 5). Although only a single key and keyway 102 have been illustrated to avoid clutter, it will be appreciated that 2, 3, 4, or more keyways 102 and corresponding keys 128 may be associated with first non-rotating catheter displacement component 100 and distal end 126 of first manipulation segment 120 respectively.

First manipulation segment 120 may be initially reversibly coupled via a removable link 140 to a second manipulation segment 130 having affixed thereto an elongate shaft 132 (selectively omitted in FIGS. 1-3 to avoid clutter) adapted to slidably and rotatably pass through a lumen associated with the first manipulation segment, the lumen of the first non-rotating catheter displacement component and second rotatable catheter displacement component, and a connected delivery catheter for a left atrial appendage occlusion device. The removable link 140 may be formed in any manner known in the art for that purpose. For example, the illustrated link 140 of FIGS. 1-3 may be a friction-fit removable link or links (140). In other embodiments, the removable link may be formed as a frangible link. In yet other embodiments, the removable link may be provided by a bayonet connector or the like.

The elongate shaft 132 may be releasably coupled at its distal end to a left atrial appendage occlusion device (not shown). In some embodiments, the distal end of elongate shaft 132 may be releasably connected to at its distal end to a left atrial appendage occlusion device by a threated segment. In other embodiments, the distal end of elongate shaft 132 may be releasably connected to at its distal end to a left atrial appendage occlusion device by other means known in the art such as a soluble link, a magnetic link, and the like.

Figure 3:
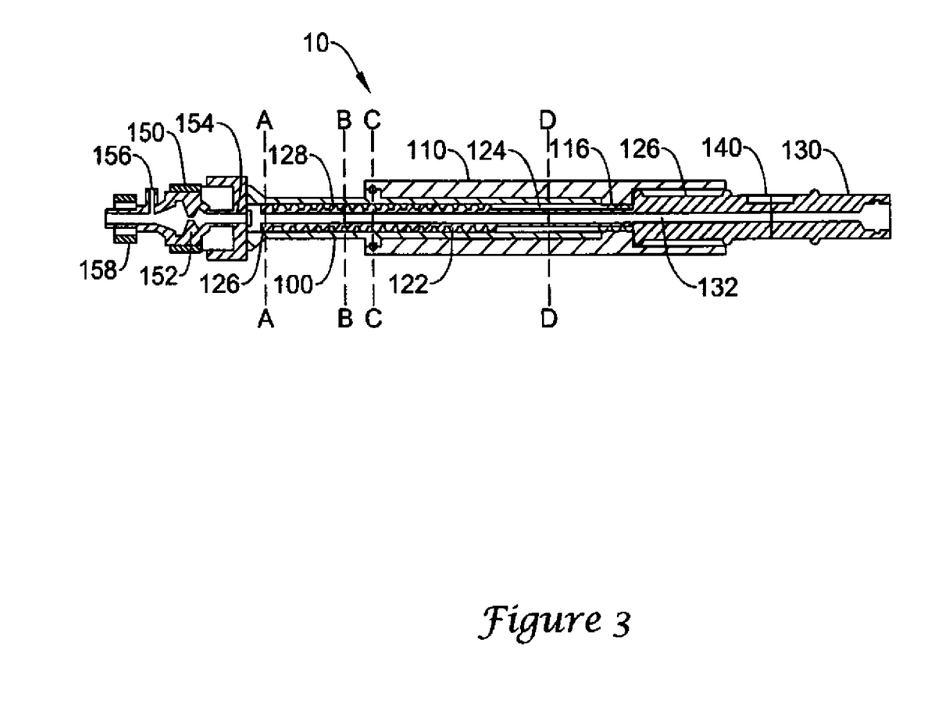
FIG. 3 illustrates the handle assembly of FIG. 1 in a second configuration in longitudinal cross-section.

As illustrated by the transition between FIGS. 2 and 3, rotation of second rotatable catheter displacement component 110 relative to first non-rotating catheter displacement component 100 and externally threaded tubular distal extension 122 of first manipulation segment 120 once the left atrial appendage is positioned within the left atrial appendage initially withdraws the delivery catheter for a left atrial appendage occlusion device, relative to elongate shaft 132 (not shown) affixed to second manipulation segment 130, by a length equal to the length of the externally threaded tubular distal extension 122 thereby ejecting the left atrial appendage occlusion device within the left atrial appendage allowing it to expand, actively or passively depending upon the device design.

If present, tubular segment 124 of first manipulation segment 120 allows the delivery catheter for a left atrial appendage occlusion device to be withdrawn an additional length. (See FIGS. 3 and 5.) The additional travel afforded by this further displacement of the delivery catheter for a left atrial appendage occlusion device relative to the elongate shaft 132 to which the left atrial appendage occlusion device is releasably coupled may serve several purposes. For example, displacing the delivery catheter for a left atrial appendage occlusion device relative to the left atrial appendage occlusion device may allow clearer visualization of the left atrial appendage occlusion device as it is deployed within the left atrial appendage, particularly if one or more of the left atrial appendage occlusion device, the elongate shaft, and the delivery catheter for a left atrial appendage occlusion device include one or more radiopaque or MRI imageable markers. The additional travel afforded by further displacement of the delivery catheter for a left atrial appendage occlusion device relative to the elongate shaft 132 may also facilitate anchoring the a left atrial appendage occlusion device by allowing it to be "tugged" relative to the left atrial appendage which may serve to seat or otherwise engage anchoring appendages, such as hooks or barbs, which may optionally be included in the left atrial appendage occlusion device.

Figure 4A:
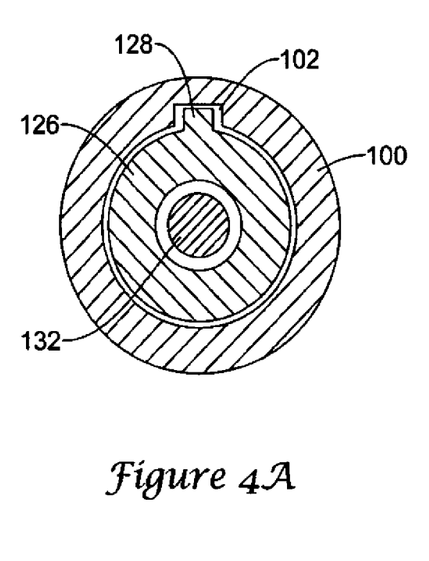
FIGS. 4A-4D illustrates the indicated transverse cross-sections the handle assembly of FIG. 1 in the second configuration.
Figure 4B:
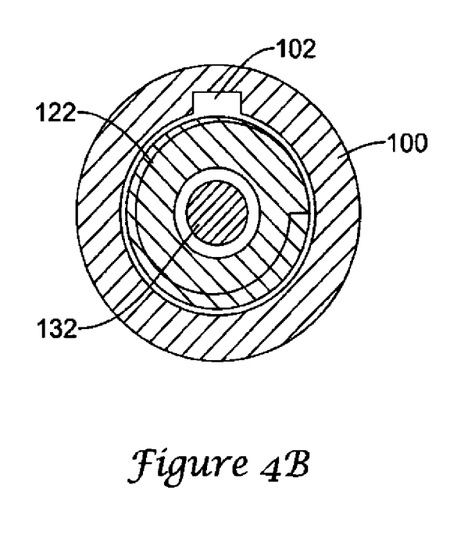

Turning to the cross-sectional views of an embodiment of the disclosed handle assembly found in FIGS. 4A-4D, FIG. 4A illustrates the distal end 126 of the externally threaded tubular distal extension 122 of first manipulation segment 120 in which key 128 engages keyway 102 of first non-rotating catheter displacement component 100. In some embodiments, distal end 126 of the externally threaded tubular distal extension 122 of first manipulation segment 120 may be sized and adapted to ensure that the externally threaded tubular distal extension 122 of first manipulation segment 120 does not translate distally beyond the distal end of the first non-rotating catheter displacement component 100. In other embodiments, distal end 126 of the externally threaded tubular distal extension 122 of first manipulation segment 120 may be sized and adapted to ensure that the externally threaded tubular distal extension 122 of first manipulation segment 120 does not translate proximally beyond the distal end of the internally threaded segment 116 of the second rotatable catheter displacement component 110. As noted herein, some embodiments may employ more than one key and keyway if desired. Elongate shaft 132 is visible within the lumen of externally threaded tubular distal extension 122 of first manipulation segment 120 which in turn is located within the lumen of first non-rotating catheter displacement component 100. FIG. 4B is similar; however the cross-section now passes through the externally threaded tubular distal extension 122.

Figure 4C:
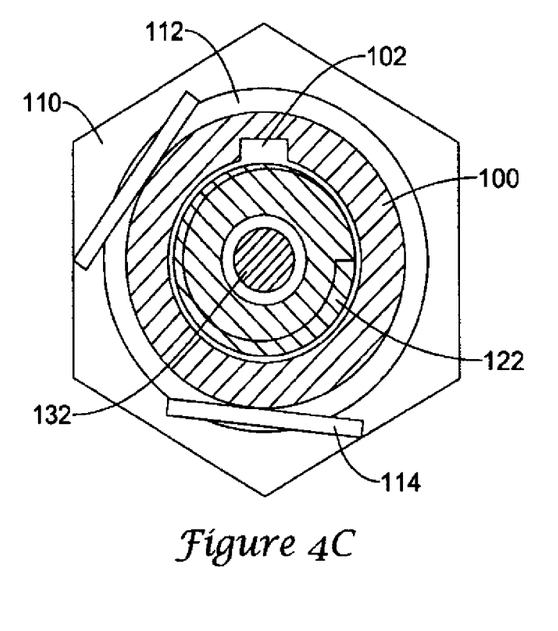

FIG. 4C passes through a join between first non-rotating catheter displacement component 100 and second rotatable catheter displacement component 110 which allows relative rotation without significant longitudinal translation. In this non-limiting embodiment, the join is formed by two flanges 112 attached to the first non-rotating catheter displacement component 100 and by one or more pins 114 affixed to the second rotatable catheter displacement component 110 and resting in the groove between the flanges 114.

Figure 4D:
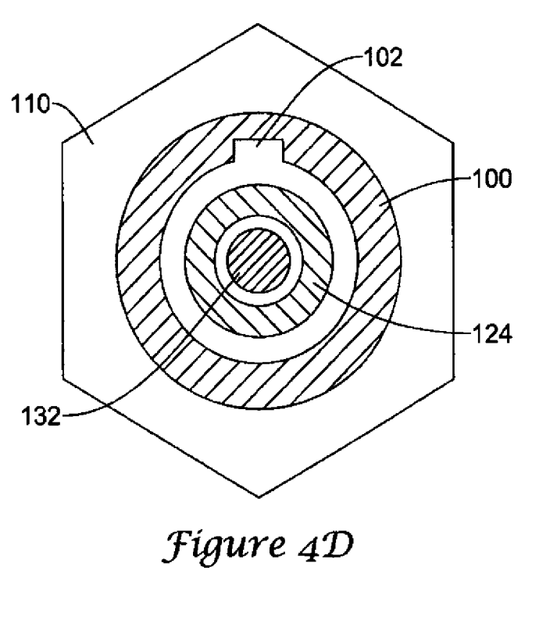

FIG. 4D illustrates a more proximal cross-section of the embodiment of FIG. 3 in which the externally threaded tubular distal extension 122 of first manipulation segment has disengaged from the internally threaded segment 116 of the second rotatable catheter displacement component 110 thereby ensuring that the left atrial appendage occlusion device has been displaced from the distal end of the delivery catheter 160 for a left atrial appendage occlusion device and the delivery catheter for a left atrial appendage occlusion device has been further withdrawn relative to the elongate shaft 132. Accordingly, the section depicted in FIG. 4D passes through tubular segment 124 of first manipulation segment 120.

As noted herein, in some embodiments, elements such as a hemostatic valve 150 may be inserted between the handle assembly 10 for a left atrial appendage occlusion device delivery system and the delivery catheter. As illustrated in FIGS. 1-3, a non-limiting hemostatic valve 150 has a seal 152, a tubular seal displacing element 154, and a fluid injection port 156. In a first configuration of the seal 150 hemostatic valve 150 slidingly and rotatably receives elongate shaft 132 while preventing pressurized fluid introduced through fluid injection port 156 during flushing of the a left atrial appendage occlusion device delivery system prior to use from leaking through the handle. In a second configuration, tubular seal displacing element 154 may be advanced through the seal, for example by tightening a housing component, to provide a bushing-type fluid seal while reducing the frictional drag on the elongate shaft 132 thereby providing the operator with enhanced feel for forces acting on the left atrial appendage occlusion device during deployment. If desired, the tubular seal displacing element 154 may be advanced and withdrawn multiple times during a procedure, for example to minimize bleed-back, if it becomes desirable to withdraw the left atrial appendage occlusion device within the delivery catheter of a left atrial appendage occlusion device delivery system for repositioning. It will be appreciated that although the illustrated embodiment combines a hemostatic valve 150 and a fluid injection port 156 in a single unit, the elements may be provided separately.

Figure 5:
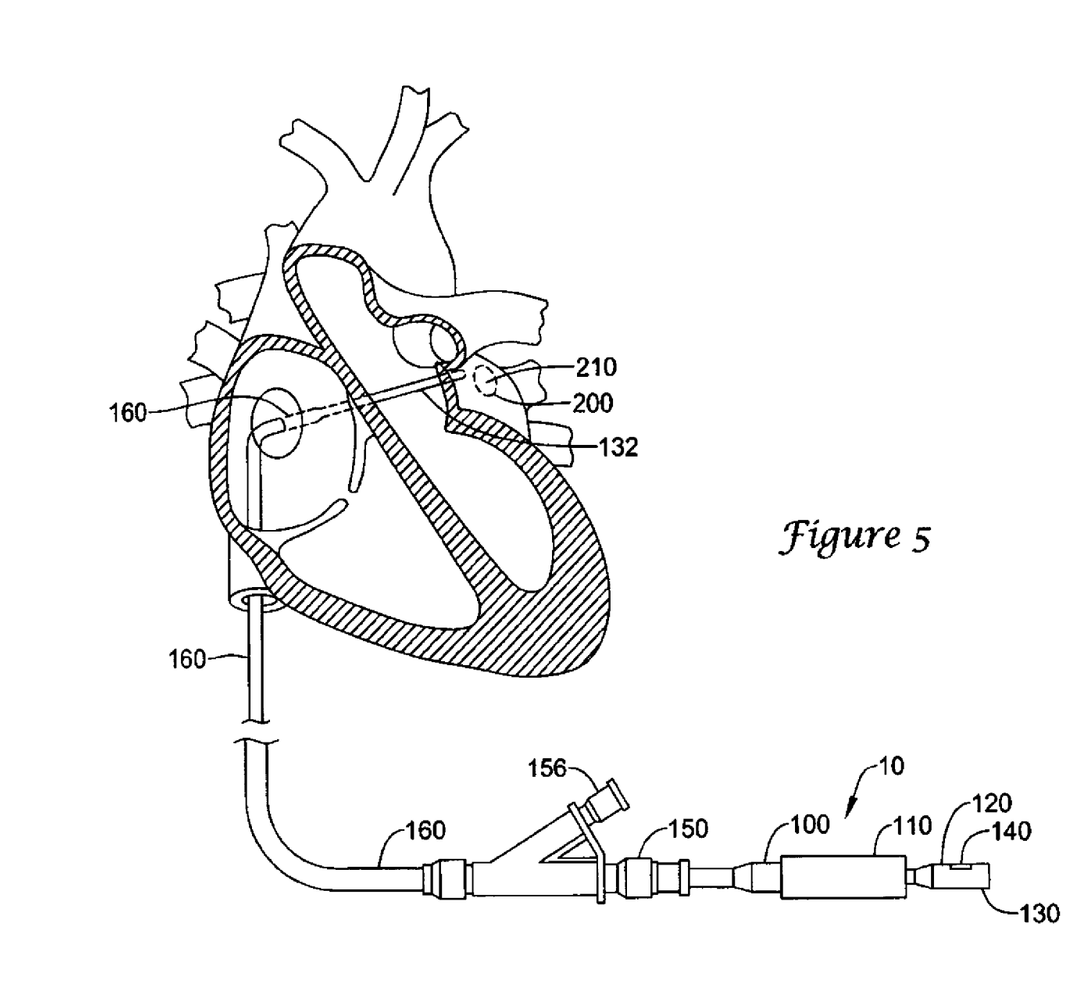
FIG. 5 illustrates a handle assembly for a left atrial appendage occlusion device delivery system as it may be used to deliver a left atrial appendage occlusion device.

The structure and operation of the disclosed handle assembly for a left atrial appendage occlusion device delivery system may be further disclosed with reference to FIG. 5 in which an exemplary handle assembly is used to deploy a known left atrial appendage occlusion device (not shown) from a delivery catheter 160 of left atrial appendage occlusion device delivery system.

Prior to use, the disclosed handle assembly 10 may be prepared for use by positioning the distal end 126 of the externally threaded tubular distal extension 122 of first manipulation segment 120 at or near the distal end of a lumen associated with first non-rotating catheter displacement component 100 and the second rotatable catheter displacement component 110 such that the distal end of elongate shaft 132 affixed to second manipulation segment 130 extends distally beyond delivery catheter 160 for a left atrial appendage occlusion device. A known left atrial appendage occlusion device (not shown) may then be reversibly attached to the distal end of elongate shaft 132. Linked first manipulation segment 120 and second manipulation segment 130 may then be withdrawn proximally to position externally threaded tubular distal extension 122 of first manipulation segment 120 adjacent internally threaded tubular distal extension 116 of second rotatable catheter displacement component 110. The known left atrial appendage occlusion device may then be collapsed and withdrawn into the distal end of delivery catheter 160 for a left atrial appendage occlusion device by rotating second rotatable catheter displacement component 110 relative to first non-rotating catheter displacement component 100, thereby engaging externally threaded tubular distal extension 122 of first manipulation segment 120 with internally threaded tubular distal extension 116 of second rotatable catheter displacement component 110, and continuing to rotate first manipulation segment 120 until distal end 126 of the externally threaded tubular distal extension 122 of first manipulation segment 120 contacts a distal end of internally threaded tubular distal extension 116 of second rotatable catheter displacement component 110. Prior to, during, and/or after withdrawing the known left atrial appendage occlusion device into the distal end of delivery catheter 160 for a left atrial appendage occlusion device, a lumen of the delivery catheter 160 for a left atrial appendage occlusion device may be flushed to remove air by supplying an appropriate fluid, such as saline, through flushing port 156 of optional hemostatic valve 150.

Once the left atrial appendage occlusion device delivery system has been prepared for use, the distal end of delivery catheter 160 for a left atrial appendage occlusion device may be inserted intravascularly into a patient in the conventional manner. The distal end of the delivery catheter 160 for a left atrial appendage occlusion device may then be advanced to the heart and further advanced trans-septally to at least partially enter the left atrial appendage.

If desired, a tubular seal displacing element 154 may be advanced through the seal 152 of hemostasis seal 150, if present, to reduce drag on elongate shaft 132 during manipulation of the left atrial appendage occlusion device thereby enhancing the operator's feel for the deployment forces. Rotation of the second rotatable catheter displacement component 110 relative to the first non-rotating catheter displacement component 100 until the externally threaded tubular distal extension 122 of first manipulation segment 120 passes distally through the internally threaded tubular distal extension 116 of second rotatable catheter displacement component 110 withdraws the delivery catheter 160 for a left atrial appendage occlusion device relative to the elongate shaft 132 and the left atrial appendage occlusion device, thereby deploying the left atrial appendage occlusion device within the left atrial appendage. The leadscrew mechanism provides mechanical advantage for easy, backlash-free smooth deployment of the left atrial appendage occlusion device.

If desired, the first manipulation segment 120 may be further advanced distally relative to the first non-rotating catheter displacement component 100, to allow the desired positioning of the left atrial appendage occlusion device within left atrial appendage to be confirmed by visualization of radiopaque or MRI imageable markers (not shown) associated with the delivery catheter 160 for a left atrial appendage occlusion device, the elongate shaft 132, and/or the left atrial appendage occlusion device. If the initial positioning is deemed to be undesirable, the first manipulation segment 120 may be withdrawn proximally relative to the first non-rotating catheter displacement component 100 and the externally threaded tubular distal extension 122 of first manipulation segment 120 may be re-engaged with the internally threaded tubular distal extension 116 of second rotatable catheter displacement component 110 to allow the left atrial appendage occlusion device to be collapsed and withdrawn within the distal end of the delivery catheter 160 for a left atrial appendage occlusion device by rotation of second rotatable catheter displacement component 110. In this manner, the left atrial appendage occlusion device may be repositioned as necessary.

Once the left atrial appendage occlusion device is properly positioned within the left atrial appendage, the first manipulation segment 120 may be tugged by the operator to seat any anchoring elements such as hooks or barbs in the tissue of the left atrial appendage. The reversible coupling 140 between first manipulation segment 120 and second manipulation segment 130 may then be decoupled allowing second manipulation segment 130 and elongate shaft 132 to rotate relative to first manipulation segment 120 and delivery catheter 160 for a left atrial appendage occlusion device or otherwise be manipulated to releasably disconnect elongate shaft 132 from the deployed left atrial appendage occlusion device. If a hemostasis valve 150 including a tubular seal displacing element 154 is present between the first non-rotating catheter displacement component 100 and the delivery catheter 160 for a left atrial appendage occlusion device, tubular seal displacing element 154 may be withdrawn relative to seal 152. The left atrial appendage occlusion device delivery system may then be removed from the patient.

Although the illustrative examples described above relate to a left atrial appendage occlusion device delivery system, other uses for the disclosed handle system are also contemplated. In such an embodiment, the associated delivery catheter and the distal end of elongate shaft 132 may be modified to accommodate a different medical device such as a stent, stent graft, or aneurysm plug.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A handle assembly for a left atrial appendage occlusion device delivery system comprising:
    a first non-rotating catheter displacement component rotatably connected to a second rotatable catheter displacement component, said a first non-rotating catheter displacement component having a distal end adapted to operably connect to a delivery catheter for a left atrial appendage occlusion device,
    wherein the first non-rotating catheter displacement component and the second rotatable catheter displacement component further comprise a lumen therethrough,
    further wherein the second rotatable catheter displacement component portion of the lumen comprises an internally threaded segment having an inner diameter;
    a first manipulation segment having a externally threaded tubular distal extension adapted to rotationally engage the internally threaded segment of the second rotatable catheter displacement component, said externally threaded tubular distal extension having a first length and a tubular segment having a second length affixed to a proximal end of the externally threaded tubular distal extension and an outer diameter smaller than the inner diameter of the internally threaded segment of the second rotatable catheter displacement component; and
    a second manipulation segment reversibly coupled to the first manipulation segment,
    wherein the second manipulation segment has affixed thereto an elongate shaft adapted to slidably and rotatably pass through a lumen associated with the first manipulation segment, the lumen of the first non-rotating catheter displacement component and second rotatable catheter displacement component, and a connected delivery catheter for a left atrial appendage occlusion device,
    further wherein rotation of the second rotatable catheter displacement component relative to the first non-rotating catheter displacement component is adapted to displace the delivery catheter proximally relative to the elongate shaft by a distance at least equal to the first length of the externally threaded tubular distal extension of the first manipulation segment,
    wherein the lumen of the first non-rotating catheter displacement component and second rotatable catheter displacement component is sized and adapted to slidably receive the externally threaded tubular distal extension of the first manipulation segment in a region distal of the internally threaded segment of the second rotatable catheter displacement component.

2. The handle assembly of claim 1, wherein the lumen of the first non-rotating catheter displacement component and second rotatable catheter displacement component is sized and adapted to slidably receive the externally threaded tubular distal extension of the first manipulation segment and at least a portion of the tubular segment of the first manipulation segment in a region distal of the internally threaded segment of the second rotatable catheter displacement component.

3. The handle assembly of any of claims 1, wherein the distal end of the lumen of the first non-rotating catheter displacement component and second rotatable catheter displacement component is sized and adapted to prevent a distal end of the externally threaded tubular distal extension of the first manipulation segment from extending distally beyond the distal end of the first non-rotating catheter displacement component.

4. The handle assembly of any of claims 1, wherein the distal end of the externally threaded tubular distal extension of the first manipulation segment is sized and adapted to prevent the distal end of the externally threaded tubular distal extension from passing proximally through the internally threaded segment of the second rotatable catheter displacement component.

5. The handle assembly of claim 1, wherein the second manipulation segment is reversibly coupled to the first manipulation segment by a removable link.

6. The handle assembly of claim 1, wherein the second manipulation segment is reversibly coupled to the first manipulation segment by bayonet connection.

7. The handle assembly of claim 1, further comprising a hemostasis valve adapted to be disposed between the delivery catheter for a left atrial appendage occlusion device and the first non-rotating catheter displacement component.

8. The handle assembly of claim 7, further comprising a tubular seal displacing element adapted to be interposed between a seal of the hemostasis valve and the elongate shaft, wherein the tubular seal displacing element has a lumen sized and adapted to allow the elongate shaft to slidably and rotatably pass therethrough while substantially preventing fluid from passing through the lumen.

9. The handle assembly of claim 1, wherein the distal end of the elongate shaft is adapted to releasably connect to a left atrial appendage occlusion device.

10. The handle assembly of claim 1, wherein the delivery catheter for a left atrial appendage occlusion device includes at the distal end thereof a region adapted to contain a left atrial appendage occlusion device in a partially collapsed delivery configuration.

11. The handle assembly of claim 10, wherein the first length of the externally threaded tubular distal extension of the first manipulation segment is at least equal to the length of a left atrial appendage occlusion device.

12. The handle assembly of claim 1, wherein the first non-rotating catheter displacement component and the externally threaded tubular distal extension of the first manipulation segment cooperate to prevent rotation of the externally threaded tubular distal extension of the first manipulation segment relative to the first non-rotating catheter displacement component.

13. The handle assembly of claim 1, wherein the tubular segment of the first manipulation segment further includes an enlarged proximal region.

* * * * *